United States Patent
Roggenkamp et al.

(10) Patent No.: US 10,064,831 B2
(45) Date of Patent: Sep. 4, 2018

(54) ACTIVE SUBSTANCES AND COSMETIC OR DERMATOLOGICAL PREPARATIONS CONTAINING SAID ACTIVE SUBSTANCES FOR THE CARE OF THE SKIN OF PATIENTS OF DIABETES MELLITUS

(71) Applicant: BEIERSDORF AG, Hamburg (DE)

(72) Inventors: Dennis Roggenkamp, Hamburg (DE); Olga Reichert, Hamburg (DE); Ludger Kolbe, Dohren (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 15/551,689

(22) PCT Filed: Feb. 8, 2016

(86) PCT No.: PCT/EP2016/052611
§ 371 (c)(1),
(2) Date: Aug. 17, 2017

(87) PCT Pub. No.: WO2016/134961
PCT Pub. Date: Sep. 1, 2016

(65) Prior Publication Data
US 2018/0036258 A1    Feb. 8, 2018

(30) Foreign Application Priority Data
Feb. 26, 2015   (DE) .................. 10 2015 203 444

(51) Int. Cl.
| | | |
|---|---|---|
| *A61K 31/121* | (2006.01) | |
| *A61K 8/06* | (2006.01) | |
| *A61K 8/96* | (2006.01) | |
| *A61Q 19/00* | (2006.01) | |
| *A61K 36/484* | (2006.01) | |
| *A61K 8/34* | (2006.01) | |
| *A61K 8/35* | (2006.01) | |

(52) U.S. Cl.
CPC ............ *A61K 31/121* (2013.01); *A61K 8/062* (2013.01); *A61K 8/064* (2013.01); *A61K 8/345* (2013.01); *A61K 8/35* (2013.01); *A61K 8/96* (2013.01); *A61K 36/484* (2013.01); *A61Q 19/007* (2013.01)

(58) Field of Classification Search
None
See application file for complete search history.

(56) References Cited

FOREIGN PATENT DOCUMENTS

| | | | | |
|---|---|---|---|---|
| CN | 104161867 A | | 11/2014 | |
| CN | 105769897 A | * | 7/2016 | ......... A61K 31/7048 |
| DE | 102012218116 A1 | | 4/2014 | |
| EP | 2695599 A1 | | 2/2014 | |
| FR | 2997626 A1 | | 5/2014 | |
| WO | 2005030157 A1 | | 7/2005 | |
| WO | WO 2008/101692 A2 | * | 8/2008 | ........... A61K 31/401 |

OTHER PUBLICATIONS

Lu, Lianwei, Acc. No. 2016:1212068 in database CAPLUS, English language abstract of CN 105769897 A (Jul. 20, 2016) accessed by CAS SciFinder.*
Anonymous: "GNPD—Intensive Soothing Cream" Jan. 1, 2015 (Jan. 1, 2015). XP055259555. Retrieved from the Internet: URL:http://www.gnpd.comjsinatrajrecordpage /2935109/from search/UlgAlYvBwD/ [retrieved on-Mar. 18, 2016].
Anonymous: "GNPD—After Sun Creme-Gel" Dec. 1, 2014 (Dec. 1, 2014). XP055259557. Retrieved from the Internet: URL:http://www.gnpd.comjsinatrajrecordpage /2863339/from search/GKYVsMbzhR/ [retrieved on-Mar. 18, 2016].

* cited by examiner

*Primary Examiner* — Brian J Davis
(74) *Attorney, Agent, or Firm* — Abel Law Group, LLP

(57) ABSTRACT

Licochalcone A and/or plant extracts or microbiologically obtained extracts with an active content of Licochalcone A or cosmetic or dermatological preparations containing Licochalcone A and/or plant extracts or microbiologically obtained extracts with an active content of Licochalcone A for the care of the skin of patients of diabetes mellitus.

17 Claims, 1 Drawing Sheet

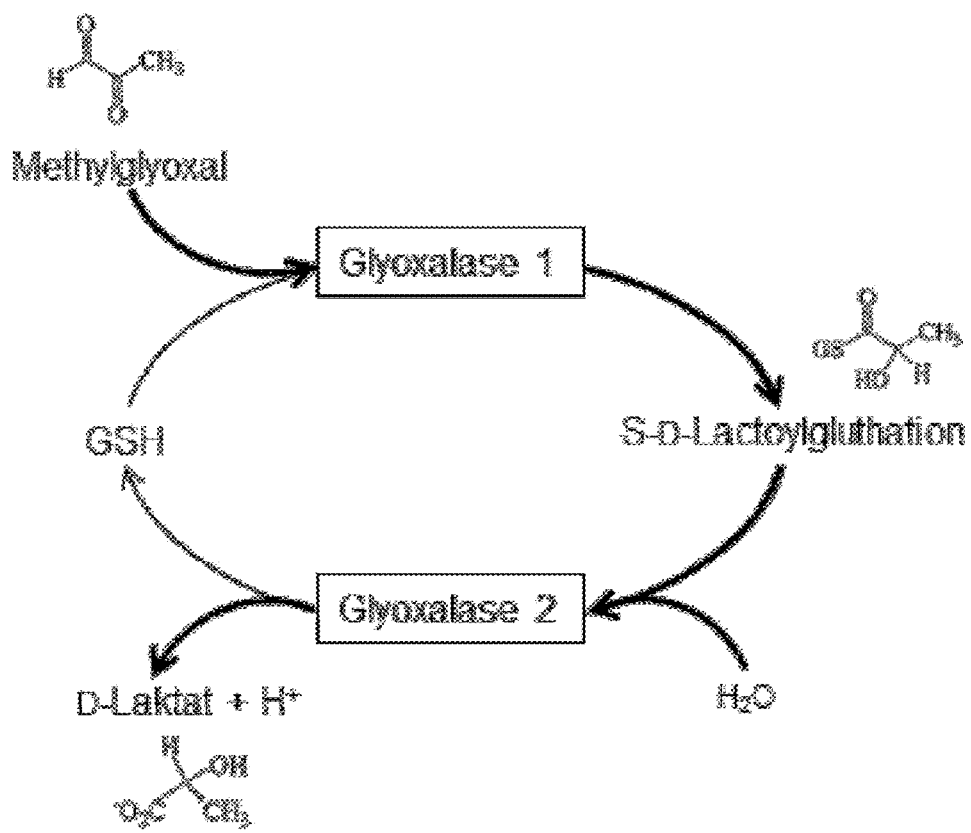
Prior Art
The detoxification of methylglyoxal by the glyoxalase system

ACTIVE SUBSTANCES AND COSMETIC OR DERMATOLOGICAL PREPARATIONS CONTAINING SAID ACTIVE SUBSTANCES FOR THE CARE OF THE SKIN OF PATIENTS OF DIABETES MELLITUS

BACKGROUND OF INVENTION

Field of the Invention

The invention relates to active substances and cosmetic or dermatological preparations containing such active substances for the care of the skin of diabetes mellitus patients.

Discussion of Background Information

Diabetes mellitus is a polyetiological metabolic disorder which leads to a chronically elevated blood glucose concentration (hyperglycemia) owing to insufficient insulin production or insulin action. The diagnosis criteria for diabetes mellitus are an elevated proportion of glycated hemoglobin ($HbA_{1c}$ value; ≥6.5%, ≥48 mM), an elevated plasma glucose concentration in the fasting state (126 mg/dl, ≥7 mM) or two hours after an oral glucose load (200 mg/dl, ≥11 mM) (American Diabetes Association, 2009).

The incidence and prevalence of this disorder is steadily rising worldwide and is 8.4% in Germany (International Diabetes Federation, 2011). Secondary complications of diabetes are seen as the main cause of the high morbidity and mortality rate. These sequelae include diabetic retinopathy, diabetic neuropathy, diabetic nephropathy, myocardial infarction and also cerebral insult (American Diabetes Association, 2009).

Diabetes is classified into the following main groups: type 1 diabetes mellitus (T1DM), type 2 diabetes mellitus (T2DM), gestational diabetes and other specific forms of diabetes (Alberti and Zimmet, 1998). In the case of diabetes mellitus type 1, there is an autoimmune-related, progressive depletion of the insulin-producing β-cells. Therefore, this form of diabetes features insulin deficiency. By contrast, in the case of the dominant type 2 diabetes mellitus, which affects about 90-95% of all diabetics, there is primarily insulin resistance of the peripheral organs and insufficient compensation in the release of insulin (American Diabetes Association, 2009). The pathological mechanisms of insulin resistance include downregulation of the insulin receptor (InsR) (Le Roith and Zick, 2001), phosphorylation of the insulin receptor substrate (IRS) (Le Roith and Zick, 2001; Paz et al., 1997) or deficient GLUT4 translocation (Brozinick et al., 2007; McCarthy et al., 2006). Genetic predisposition, poor diet and lack of physical activity are seen to cause the manifestation of type 2 diabetes.

Epidemiologically, about 30% of diabetes mellitus patients develop various skin complications over the course of their disorder (Gkogkolou and Böhm, 2014; Perez and Kohn, 1994). Since the cutaneous complications already manifest before the diagnosis of diabetes, their diagnostic relevance is currently under discussion. Cutaneous infections are among the most common diabetes-associated skin disorders. In this connection, diabetic patients suffer cumulatively from bacterial and mycotic skin infections (Perez and Kohn, 1994). A likewise characteristic skin symptom in diabetics is diabetic dermopathy.

It is distinguished by hyperpigmented and, in some cases, atrophic lesions on the lower limbs (Morgan and Schwartz, 2008). Further diabetes-associated skin manifestations include necrobiosis lipoidica, acanthosis nigricans, vitiligo and chronic pruritus (Behm et al., 2012; Gkogkolou and Böhm, 2014). Among the most clinically significant diabetic skin complications, with a high morbidity and mortality rate, is diabetic foot (Gkogkolou and Böhm, 2014). The pathogenesis of this diabetic sequela is highly complex and combines the appearance of various diabetic secondary complications, such as microangiopathy and macroangiopathy, neuropathy, wound-healing deficiencies and skin infections (Karrer, 2011).

In this connection, the diabetes-induced skin changes arise either as a result of primary diabetes-induced changes in cell metabolism or as a result of acquired diabetes-associated complications, such as, for example, diabetic vasculopathy and diabetic neuropathy (Perez and Kohn, 1994). Diabetic neuropathy is a dysfunction of the peripheral nervous system that is caused by diabetes mellitus and is among the most prevalent long-term diabetic complications (Vinik et al., 2000). The skin is affected too by the impairment of the peripheral nervous system and has a hypoinnervated state (Kennedy et al., 1996; Shun et al., 2004).

The consequences of cutaneous hypoinnervation include impaired perception, reduced productivity of the sweat glands (anhidrosis), dry skin (xerosis cutis) (Poretsky and Liao, 2013), impaired wound healing (Barker et al., 2006; Fukai et al., 2005) and impaired epidermal homeostasis (Hsieh and Lin, 1999). Thus, diabetic neuropathy is one of the central inducers of the diabetic skin complications (Gkogkolou and Böhm, 2014). While the clinical involvement of the skin in the context of diabetes has been described very well, the precise molecular mechanisms leading to the skin complications are, however, unknown to a very great extent.

Methylglyoxal (MGO) is a reactive α-oxoaldehyde and a physiological metabolite of glycolysis. It contains a keto group and an aldehyde group and is, with a molecular weight of 72 Da, defined as a small molecule. MGO is a highly reactive molecule and the key inducer of AGEs (Thornalley, 1993).

In this connection, MGO differs very significantly from glucose with respect to the glycation reaction. Glucose reacts with proteins mainly via lysine residues or N-terminal amino groups. By contrast, MGO reacts predominantly with arginine residues of proteins and forms MGO-hydroimidazolone (MGO-H1), which is one of the most relevant AGEs in vivo (Ahmed et al., 2003). As a consequence, functional dysfunctions in the thus modified proteins are much more likely, since arginine residues occur more frequently than lysine residues in functional protein domains (Thornalley and Rabbani, 2011).

In living organisms, the formation of methylglyoxal is induced by various metabolic processes. In this connection, the most common and most important source is glycolysis. Nonenzymatic elimination of the phosphate group of glyceraldehyde 3-phosphate (G3P) and dihydroxyacetone phosphate (DHAP) thus gives rise to MGO (Phillips and Thornalley, 1993).

Owing to the reactive nature of methylglyoxal, cells have a natural detoxification mechanism for eliminating the cytotoxic molecule as rapidly as possible. In this connection, MGO is mainly converted to harmless D-lactate with the aid of the glyoxalase system. The glyoxalase system consists of the enzymes glyoxalase 1 and glyoxalase 2.

The attached FIGURE depicts the degradation mechanism. MGO reacts with GSH and forms a hemithioacetal. Said hemithioacetal is converted to S-D-lactoylglutathione. This reaction is catalyzed by glyoxalase 1 and requires catalytic amounts of GSH. The second reaction step is catalyzed by glyoxalase 2 and involves the further metabolization to form D-lactate and to regenerate GSH (Thornalley, 1990).

Methylglyoxal reacts with GSH (glutathione) to form the hemithioacetal and is degraded in a two-step enzymatic reaction by glyoxalase 1 and glyoxalase 2 via S-D-lactoylglutathione to form harmless lactate. Modified according to (Rabbani and Thornalley, 2014).

In diabetic patients, the plasma concentration of MGO is elevated two- to four-fold and thus so is the formation of MGO-derived AGEs (Bierhaus et al., 2012; Han et al., 2007; Nakayama et al., 2008). The MGO-induced formation of AGEs can even turn out disproportionally higher, since GLO1 exhibits dysfunctions in diabetics (Bierhaus et al., 2012; Jack et al., 2011; Skapare et al., 2013). On the basis of these findings, an important role is attributed to MGO in the development of various diabetic secondary complications, such as, for example, neuropathy (Bierhaus et al., 2012; Eberhardt et al., 2012) and nephropathy (Beisswenger et al., 2005).

In summary, it can thus be stated that the diabetic skin suffers from a multiplicity of impairments (dryness, pruritus, impaired wound healing, reduced skin sensation, and infections), which may also occur in other skin conditions, but never as severely and concentratedly as in diabetes.

The customary skin-moisturizing care products, which contain much glycerol, are excellent for the normal skin, but do not solve the problems of the diabetic skin.

SUMMARY OF THE INVENTION

It is thus an object of the invention to find an approach which makes it possible to treat the diabetic skin problems more specifically and thus more effectively.

It was found that, surprisingly, licochalcone A induces in skin cells an enhanced activity of glyoxalases, which detoxify the methylglyoxal that forms to a great extent in diabetes. This significantly reduces the oxidative and inflammatory stress in the diabetic skin and, as a result, allows a substantial improvement in this specific skin condition.

Therefore, according to the invention, licochalcone A and/or plant extracts or microbiologically obtained extracts having an effective content of licochalcone A, or cosmetic or dermatological preparations containing licochalcone A and/or plant extracts or microbiologically obtained extracts having an effective content of licochalcone A, are for the care of the skin of diabetes mellitus patients.

In particular, it is advantageous when the cosmetic or dermatological preparations according to the invention contain from 0.0001 to 5% by weight, more particularly from 0.001 to 1% by weight, very particularly from 0.005 to 0.15% by weight, of licochalcone A, based on the total weight of the preparation.

Furthermore, what is advantageous in particular is the use according to the invention, characterized in that the preparations contain from 0.001 to 10% by weight, more particularly from 0.05 to 5% by weight, very particularly from 0.01 to 2% by weight, of one or more polyols, based on the total weight of the preparation.

Furthermore, what is advantageous in particular is the use according to the invention, characterized in that the preparations contain licochalcone as constituent of plant extracts, more particularly of *Radix Glycyrrhizae inflatae*.

The plant species *Glycyrrhiza inflata* belongs, like the Europe-official licorice *Glycyrrhiza glabra*, to the genus *Glycyrrhiza*, which belongs to the Fabaceae (pea) plant family. The drug *Radix Glycyrrhizae inflatae*, i.e., the root of the plant, is in use, for example in Far East medicine. The use of the drug as anti-inflammatory is likewise known.

A constituent of the aqueous extract from *Radix Glycyrrhizae inflatae* is licochalcone A, which is distinguished by the following structural formula:

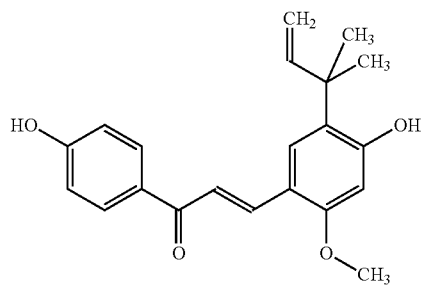 [SMILES: C=CC(C)(C)c1cc(/C=C/C(=O)c2ccc(O)cc2)c(OC)cc1O]

It is assumed that this substance, possibly in synergy with the other constituents of the extract, has a share of the action according to the invention.

It is advantageous according to the invention when the cosmetic or dermatological preparations contain from 0.001 to 10% by weight, more particularly from 0.05 to 5% by weight, very particularly from 0.01 to 2% by weight, of an aqueous extract from *Radix Glycyrrhizae inflatae*, based on the total weight of the preparation.

It is advantageous according to the invention when the cosmetic or dermatological preparations contain from 0.001 to 10% by weight, more particularly from 0.05 to 5% by weight, very particularly from 0.01 to 2% by weight, of one or more ethoxylated or propoxylated raw materials, based on the total weight of the preparation.

It is advantageous according to the invention when the cosmetic or dermatological preparations contain from 0.001 to 10% by weight, more particularly from 0.05 to 5% by weight, very particularly from 0.01 to 2% by weight, of one or more polyols, based on the total weight of the preparation.

In particular, it is advantageous to select butylene glycol as polyol.

It is very particularly advantageous to proceed from an extract sold under the name Polyol Soluble Licorice Extract P-U by Maruzen.

Furthermore, it is advantageous to use licochalcone A in other vehicle systems in a concentration from 0.0001 to 5% by weight, more particularly from 0.001 to 1% by weight, very particularly from 0.005 to 0.05% by weight.

According to the invention, customary antioxidants can be used preparations containing the active-substance combinations according to the invention.

The amount of antioxidants (one or more compounds) in the preparations is preferably from 0.001 to 30% by weight, particularly preferably from 0.05 to 20% by weight, more particularly from 1 to 10% by weight, based on the total weight of the preparation.

The prophylaxis or the cosmetic or dermatological treatment with the active substance used according to the invention or with the cosmetic or topical dermatological preparations having an effective content of active substance used according to the invention is done in the customary manner, specifically in such a way that the active substance used according to the invention or the cosmetic or topical dermatological preparations having an effective content of active substance used according to the invention is/are applied to the skin sites affected.

Advantageously, the active substance used according to the invention can be incorporated into customary cosmetic and dermatological preparations, which can be present in various forms. For example, they can be a solution, an emulsion of the type water-in-oil (W/O) or of the type oil-in-water (O/W), or a multiple emulsion, for example of the type water-in-oil-in-water (W/O/W) or oil-in-water-in-oil (O/W/O), a hydrodispersion or lipodispersion, a gel, a solid stick or else an aerosol.

Emulsions according to the invention in the context of the present invention, for example in the form of a cream, a lotion, a cosmetic milk, are advantageous and contain, for example, fats, oils, waxes and/or other lipids and also water and one or more emulsifiers, as are customarily used for this type of formulation.

It is also possible and advantageous in the context of the present invention to incorporate the active substance used according to the invention in aqueous systems or surfactant preparations for the cleansing of the skin and the hair.

It is of course known to a person skilled in the art that sophisticated cosmetic compositions are in most cases inconceivable without the customary excipients and additives. These include, for example, consistency enhancers, fillers, perfume, dyes, emulsifiers, additional active substances such as vitamins or proteins, light stabilizers, stabilizers, insect repellents, alcohol, water, salts, antimicrobial, proteolytic or keratolytic substances, etc.

Applicable mutatis mutandis are corresponding requirements for the formulation of medicinal preparations.

Medicinal topical compositions in the context of the present invention generally contain one or more medicaments in an effective concentration. For the sake of simplicity, reference is made to the legal provisions of the Federal Republic of Germany for the clear distinction between cosmetic and medicinal use and corresponding products (e.g., Kosmetikverordnung [cosmetics regulation], Lebensmittelgesetz [food act] and Arzneimittelgesetz [medicines act]).

It is in this connection likewise advantageous to add the active substance used according to the invention, as additive, to preparations which already contain other active substances for other purposes.

Accordingly, cosmetic or topical dermatological compositions in the context of the present invention can, for example, be used as skin-protection cream, cleansing milk, sun-protection lotion, nutrient cream, day cream or night cream, etc., depending on their composition. Where appropriate, it is possible and advantageous to use the compositions according to the invention as basis for pharmaceutical formulations.

Also possibly advantageous are those cosmetic and dermatological preparations present in the form of a sunscreen. Preferably, these contain not only the active substance used according to the invention, but also at least one UVA filter and/or at least one UVB filter and/or at least one inorganic pigment.

However, it is also advantageous in the context of the present inventions to create those cosmetic and dermatological preparations, the main purpose of which is not protection from sunlight, but which nevertheless contain a content of UV protective substances. For example, UV-A filters and/or UV-B filters are usually incorporated into day creams.

Advantageously, preparations according to the invention can contain substances which absorb UV radiation within the UVB region, the total amount of filter substances being, for example, from 0.1% by weight to 30% by weight, preferably from 0.5 to 10% by weight, more particularly from 1 to 6% by weight, based on the total weight of the preparations.

The cosmetic and dermatological preparations according to the invention can contain cosmetic active substances, cosmetic excipients and/or cosmetic additives, as are customarily used in such preparations, for example antioxidants, preservatives, bactericides, perfumes, antifoams, dyes, pigments having a coloring action, thickeners, surface-active substances, emulsifiers, emollient, moisturizing and/or humectant substances, fats, oils, waxes or other customary constituents of a cosmetic or dermatological formulation such as alcohols, polyols, polymers, foam stabilizers, electrolytes, organic solvents or silicone derivatives.

If the cosmetic or dermatological preparation in the context of the present invention is a solution or emulsion or dispersion, it is possible to use as solvent:

water or aqueous solutions;
oils, such as triglycerides of capric acid or of caprylic acid, but preferably castor oil;
fats, waxes and other natural and synthetic lipids, preferably esters of fatty acids with alcohols of low carbon number, for example with isopropanol, propylene glycol or glycerol, or esters of fatty alcohols with alkanoic acids of low carbon number or with fatty acids;
alcohols, diols or polyols of low carbon number, and also the ethers thereof, preferably ethanol, isopropanol, propylene glycol, glycerol, ethylene glycol, ethylene glycol monoethyl ether or ethylene glycol monobutyl ether, propylene glycol monomethyl ether, propylene glycol monoethyl ether or propylene glycol monobutyl ether, diethylene glycol monomethyl ether or diethylene glycol monoethyl ether and analogous products.

In particular, mixtures of the aforementioned solvents are used. In the case of alcoholic solvents, water can be a further constituent.

The oil phase of the emulsions, oleogels or hydrodispersions or lipodispersions in the context of the present invention is advantageously selected from the group of esters of saturated and/or unsaturated, branched and/or unbranched alkanecarboxylic acids of a chain length of from 3 to 30 carbon atoms and saturated and/or unsaturated, branched and/or unbranched alcohols of a chain length of from 3 to 30 carbon atoms, from the group of esters of aromatic carboxylic acids and saturated and/or unsaturated, branched and/or unbranched alcohols of a chain length of from 3 to 30 carbon atoms. In this case, such ester oils can be advantageously selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, for example jojoba oil. Furthermore, the oil phase can advantageously be selected from the group of branched and unbranched hydrocarbons and hydrocarbon waxes, of silicone oils, of dialkyl ethers, the group of saturated or unsaturated, branched or unbranched alcohols, and of fatty acid triglycerides, namely the triglycerol esters of saturated and/or unsaturated, branched and/or unbranched alkanecarboxylic acids of a chain length of from 8 to 24, more particularly 12-18, carbon atoms. For example, the fatty acid triglycerides can advantageously be selected from the group of synthetic, semisynthetic and natural oils, for example olive oil, sunflower oil, soybean oil, arachis oil, rapeseed oil, almond oil, palm oil, coconut oil, palm kernel oil and the like.

Any desired mixtures of such oil and wax components can advantageously be used too in the context of the present invention. Where appropriate, it may also be advantageous to use waxes, for example cetyl palmitate, as the sole lipid component of the oil phase.

Advantageously, the oil phase is selected from the group 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride, dicaprylyl ether.

Mixtures of $C_{12-15}$-alkyl benzoate and 2-ethylhexyl isostearate, mixtures of $C_{12-15}$-alkyl benzoate and isotridecyl isononanoate and also mixtures of $C_{12-15}$-alkyl benzoate, 2-ethylhexyl isostearate and isotridecyl isononanoate are particularly advantageous.

From the hydrocarbons, paraffin oil, squalane and squalene can advantageously be used in the context of the present invention.

Advantageously, the oil phase can further comprise a content of cyclic or linear silicone oils or entirely consist of such oils, though preference is given to using, besides the silicone oil(s), an additional content of other oil-phase components.

Advantageously, cyclomethicone (octamethylcyclotetrasiloxane) is used as silicone oil to be used according to the invention. But other silicone oils too can advantageously be used in the context of the present invention, for example hexamethylcyclotrisiloxane, polydimethylsiloxane, poly(methylphenylsiloxane). Furthermore, mixtures of cyclomethicone and isotridecyl isononanoate and of cyclomethicone and 2-ethylhexyl isostearate are particularly advantageous.

Where appropriate, the aqueous phase of the preparations according to the invention advantageously contains alcohols, diols or polyols of low carbon number, and the ethers thereof, preferably ethanol, isopropanol, propylene glycol, glycerol, ethylene glycol, ethylene glycol monoethyl ether or ethylene glycol monobutyl ether, propylene glycol monomethyl ether, propylene glycol monoethyl ether or propylene glycol monobutyl ether, diethylene glycol monomethyl ether or diethylene glycol monoethyl ether and analogous products, additionally alcohols of low carbon number, for example ethanol, isopropanol, 1,2-propanediol, glycerol, and also especially one or more thickeners, which can advantageously be selected from the group silicon dioxide, aluminum silicates, polysaccharides and the derivatives thereof, for example hyaluronic acid, xanthan gum, hydroxypropylmethylcellulose, particularly advantageously from the group of polyacrylates, preferably a polyacrylate from the group of so-called carbopols, for example carbopols of the types 980, 981, 1382, 2984, 5984, each on its own or in combination.

Gels used according to the invention customarily contain alcohols of low carbon number, for example ethanol, isopropanol, 1,2-propanediol, glycerol and water or an aforementioned oil in the presence of a thickener, which is preferably silicon dioxide or an aluminum silicate in the case of oily/alcoholic gels and is preferably a polyacrylate in the case of aqueous/alcoholic or alcoholic gels.

Solid sticks contain, for example, natural or synthetic waxes, fatty alcohols or fatty acid esters.

Customary basic materials suitable for use as cosmetic sticks in the context of the present invention are liquid oils (e.g., paraffin oils, castor oil, isopropyl myristate), semisolid constituents (e.g., Vaseline, lanolin), solid constituents (e.g., beeswax, ceresin and microcrystalline waxes or ozokerite) and high-melting point waxes (e.g., carnauba wax, candelilla wax).

Cosmetic preparations in the context of the present invention can also be present as gels which contain not only an effective content of active substance according to the invention and solvents customarily used therefor, preferably water, but also organic thickeners, for example gum arabic, xanthan gum, sodium alginate, cellulose derivatives, preferably methylcellulose, hydroxymethylcellulose, hydroxyethylcellulose, hydroxypropylcellulose, hydroxypropylmethylcellulose, or inorganic thickeners, for example aluminum silicates such as, for example, bentonites, or a mixture of polyethylene glycol and polyethylene glycol stearate or polyethylene glycol distearate. The thickener is present in the gel in, for example, an amount between 0.1 and 30% by weight, preferably between 0.5 and 15% by weight.

BRIEF DESCRIPTION OF THE DRAWING

In the accompanying drawing,
The FIGURE depicts the detoxification of methylglyoxal by the glyoxalase system.

DETAILED DESCRIPTION OF EMBODIMENTS OF THE INVENTION

The following examples are intended to illustrate the present invention without limiting it. Unless otherwise specified, all quantities, proportions and percentages are based on the weight and the total amount or on the total weight of the preparations.

Examples of O/W Creams

Example No. 1

| | |
|---|---|
| Glyceryl stearate, self-emulsifying | 4.00 |
| PEG-40 stearate | 1.00 |
| Cetyl alcohol | 3.00 |
| Caprylic/capric triglyceride | 5.00 |
| Paraffinum liquidum | 5.00 |
| Polyol Soluble Licorice Extract P-U | 0.025 |
| Tocopherol | 0.1 |
| Na$_3$HEDTA | 0.1 |
| Preservative, perfume | q.s. |
| Polyacrylic acid | 3.00 |
| Sodium hydroxide solution, 45% | q.s |
| Glycerol | 5.00 |
| Water | to 100 |

Example No. 2

| | |
|---|---|
| Glyceryl stearate, self-emulsifying | 3.00 |
| Stearic acid | 1.00 |
| Cetyl alcohol | 2.00 |
| Caprylic/capric triglyceride | 3.00 |
| Dicaprylyl ether | 4.00 |
| Paraffinum liquidum | 2.00 |
| Polyol Soluble Licorice Extract P-U | 0.05 |
| Preservative, perfume | q.s. |
| Polyacrylic acid | 0.1 |
| Sodium hydroxide solution, 45% | q.s |

Example No. 3 -continued

| | |
|---|---|
| Glycerol | 3.00 |
| Butylene glycol | 3.00 |
| Water | to 100 |

Example No. 3

| | |
|---|---|
| Glyceryl stearate citrate | 2.00 |
| Stearyl alcohol | 2.00 |
| Lanolin alcohol | 1.00 |
| Caprylic/capric triglyceride | 4.00 |
| Paraffinum liquidum | 8.00 |
| Dimethicone | 1.00 |
| Licochalcone A | 0.025 |
| Preservative, perfume | q.s. |
| Sodium hydroxide solution, 45% | q.s |
| Glycerol | 7.50 |
| Water | to 100 |

Example No. 4

| | |
|---|---|
| Glyceryl stearate citrate | 2.00 |
| Stearyl alcohol | 2.00 |
| Lanolin alcohol | 1.00 |
| Caprylic/capric triglyceride | 4.00 |
| Paraffinum liquidum | 8.00 |
| Dimethicone | 1.00 |
| Polyol Soluble Licorice Extract P-U | 0.15 |
| Preservative, perfume | q.s. |
| Sodium hydroxide solution, 45% | q.s |
| Glycerol | 7.50 |
| Dihydroxyacetone | 1.00 |
| Water | to 100 |

Example No. 5

| | |
|---|---|
| Polyglyceryl-3 methylglucose distearate | 3.00 |
| Cetyl alcohol | 3.00 |
| Caprylic/capric triglyceride | 3.00 |
| Dicaprylyl ether | 2.00 |
| Paraffinum liquidum | 3.00 |
| Polyol Soluble Licorice Extract P-U | 1.00 |
| Na$_3$HEDTA | 0.1 |
| Preservative, perfume | q.s. |
| Polyacrylic acid | 0.1 |
| Sodium hydroxide solution, 45% | q.s |
| Glycerol | 3.00 |
| Water | to 100 |

Example No. 6

| | |
|---|---|
| Glyceryl stearate citrate | 2.00 |
| Sorbitan stearate | 2.00 |
| Cetyl stearyl alcohol | 2.00 |
| Caprylic/capric triglyceride | 3.00 |
| Octyldodecanol | 2.00 |
| Dicaprylyl ether | 1.00 |
| Polyol Soluble Licorice Extract P-U | 0.05 |
| Tocopherol | 0.20 |
| Preservative, perfume | q.s. |
| Polyacrylic acid | 0.1 |

-continued

| | |
|---|---|
| Sodium hydroxide solution, 45% | q.s |
| Glycerol | 3.00 |
| Water | to 100 |

Examples of O/W Creams

Example No. 7

| | |
|---|---|
| Glyceryl stearate, self-emulsifying | 5.00 |
| Stearyl alcohol | 2.00 |
| Caprylic/capric triglyceride | 2.00 |
| Octyldodecanol | 2.00 |
| Dimethicone polydimethylsiloxane | 2.00 |
| Titanium dioxide | 2.00 |
| 4-Methylbenzylidene camphor | 1.00 |
| Butyl methoxydibenzoylmethane | 0.50 |
| Licochalcone A | 0.08 |
| Preservative, perfume | q.s. |
| Polyacrylic acid | 0.15 |
| Sodium hydroxide solution, 45% | q.s |
| Glycerol | 3.00 |
| Water | to 100 |

Example No. 8

| | |
|---|---|
| Glyceryl stearate citrate | 2.00 |
| Cetyl stearyl alcohol | 3.00 |
| C$_{12-15}$ alkyl benzoate | 2.00 |
| Octyldodecanol | 2.00 |
| Paraffinum liquidum | 4.00 |
| Polyol Soluble Licorice Extract P-U | 0.50 |
| 2,4-Bis[4-(2-ethylhexyloxy)-2-hydroxylphenyl]-6-(4-methoxyphenyl)-1,3,5-triazine | 1.0 |
| Dihydroxyacetone | 0.5 |
| Preservative, perfume | q.s. |
| Polyacrylic acid | 0.1 |
| Sodium hydroxide solution, 45% | q.s |
| Butylene glycol | 3.00 |
| Ethanol | 3.00 |
| Water | to 100 |

Example No. 9

| | |
|---|---|
| Glyceryl stearate citrate | 2.00 |
| Cetyl stearyl alcohol | 1.00 |
| C$_{12-15}$ alkyl benzoate | 3.00 |
| Paraffinum liquidum | 2.00 |
| Polyol Soluble Licorice Extract P-U | 0.1 |
| 2,4-Bis[4-(2-ethylhexyloxy)-2-hydroxylphenyl]-6-(4-methoxyphenyl)-1,3,5-triazine | 3.0 |
| Ethylenediaminetetraacetic acid, trisodium | 0.20 |
| Preservative, perfume | q.s. |
| Xanthan gum | 0.20 |
| Sodium hydroxide solution, 45% | q.s |
| Glycerol | 3.00 |
| Water | to 100 |

Example No. 10

| | |
|---|---|
| Stearic acid | 2.50 |
| Cetyl alcohol | 3.00 |
| Octyldodecanol | 4.00 |

-continued

| | |
|---|---|
| Cyclic dimethyl polysiloxane | 0.50 |
| Polyol Soluble Licorice Extract P-U | 1.00 |
| Preservative, perfume | q.s. |
| Polyacrylic acid | 0.05 |
| Sodium hydroxide solution, 45% | q.s |
| Glycerol | 5.00 |
| Ethanol | 3.00 |
| Water | to 100 |

Example No. 11

| | |
|---|---|
| Stearic acid | 3.50 |
| Cetyl alcohol | 4.50 |
| Cetyl stearyl alcohol | 0.50 |
| Octyldodecanol | 6.00 |
| Cyclic dimethyl polysiloxane | 2.00 |
| 4-Methylbenzylidene camphor | 1.00 |
| Butyl methoxydibenzoylmethane | 0.50 |
| Polyol Soluble Licorice Extract P-U | 0.40 |
| 2,4-Bis[4-(2-ethylhexyloxy)-2-hydroxylphenyl]-6-(4-methoxyphenyl)-1,3,5-triazine | 0.5 |
| Dihydroxyacetone | 0.5 |
| Tocopherol | 0.05 |
| Ethylenediaminetetraacetic acid, trisodium | 0.20 |
| Preservative, perfume | q.s. |
| Polyacrylic acid | 0.05 |
| Sodium hydroxide solution, 45% | q.s |
| Glycerol | 3.00 |

Examples of W/O Emulsions

Example No. 12

| | |
|---|---|
| Polyglyceryl-2 dipolyhydroxystearate | 5.00 |
| 2,4-Bis[4-(2-ethylhexyloxy)-2-hydroxylphenyl]-6-(4-methoxyphenyl)-1,3,5-triazine | 2.00 |
| Diethylhexyl butamido triazone | 3.00 |
| Octocrylene | 7.00 |
| Diethylhexyl butamido triazone | 1.00 |
| Phenylene-1,4-bis(monosodium)-2-benzimidazyl-5,7-disulfonic acid | 1.00 |
| Phenylbenzimidazole sulfonic acid | 0.50 |
| Zinc oxide | 3.00 |
| Dicaprylyl ether | 10.00 |
| Dicaprylyl carbonate | 5.00 |
| Phenyl methylpolysiloxane | 2.00 |
| PVP hexadecene copolymer | 0.50 |
| Glycerol | 3.00 |
| Magnesium sulfate | 1.00 |
| Tocopheryl acetate | 0.50 |
| Polyol Soluble Licorice Extract P-U | 0.15 |
| Preservative, perfume | q.s. |
| Ethanol | 3.00 |
| Water | to 100 |

Example No. 13

| | |
|---|---|
| Cetyl dimethicone copolyol | 2.50 |
| 2-Ethylhexyl methoxycinnamate | 8.00 |
| 2,4-Bis[4-(2-ethylhexyloxy)-2-hydroxylphenyl]-6-(4-methoxyphenyl)-1,3,5-triazine | 2.50 |
| Diethylhexyl butamido triazone | 1.00 |
| 4-Methylbenzylidene camphor | 2.00 |
| Octocrylene | 2.50 |

-continued

| | |
|---|---|
| Phenylene-1,4-bis(monosodium)-2-benzimidazyl-5,7-disulfonic acid | 2.00 |
| Titanium dioxide | 2.00 |
| Zinc oxide | 1.00 |
| Dimethicone polydimethylsiloxane | 4.00 |
| Phenyl methylpolysiloxane | 25.00 |
| Octoxyglycerol | 0.30 |
| Glycerol | 7.50 |
| Glycine soybean oil | 1.00 |
| Magnesium sulfate | 0.50 |
| Polyol Soluble Licorice Extract P-U | 0.08 |
| Preservative, perfume | q.s. |
| Water | to 100 |

Example No. 14

| | |
|---|---|
| PEG-30 dipolyhydroxystearate | 5.00 |
| Butyl methoxydibenzoylmethane | 2.00 |
| Ethylhexyl triazone | 3.00 |
| Octocrylene | 4.00 |
| Phenylene-1,4-bis(monosodium)-2-benzimidazyl-5,7-disulfonic acid | 0.50 |
| Titanium dioxide | 1.50 |
| Zinc oxide | 2.00 |
| Paraffinum liquidum | 10.0 |
| Butylene glycol dicaprylate/dicaprate | 2.00 |
| Dicaprylyl carbonate | 6.00 |
| Dimethicone polydimethylsiloxane | 1.00 |
| Shea butter | 3.00 |
| Octoxyglycerol | 1.00 |
| Glycine soybean oil | 1.50 |
| Magnesium chloride | 1.00 |
| Tocopheryl acetate | 0.25 |
| Polyol Soluble Licorice Extract P-U | 0.5 |
| Preservative, perfume | q.s. |
| Ethanol | 1.50 |
| Water | to 100 |

Example No. 15

| | |
|---|---|
| Cetyl dimethicone copolyol | 4.00 |
| 2-Ethylhexyl methoxycinnamate | 5.00 |
| 2,4-Bis[4-(2-ethylhexyloxy)-2-hydroxylphenyl]-6-(4-methoxyphenyl)-1,3,5-triazine | 2.00 |
| Butyl methoxydibenzoylmethane | 1.00 |
| Ethylhexyl triazone | 4.00 |
| 4-Methylbenzylidene camphor | 4.00 |
| Diethylhexyl butamido triazone | 2.00 |
| Phenylbenzimidazole sulfonic acid | 3.00 |
| Zinc oxide | 0.50 |
| $C_{12-15}$ alkyl benzoate | 9.00 |
| Butylene glycol dicaprylate/dicaprate | 8.00 |
| Dimethicone polydimethylsiloxane | 5.00 |
| PVP hexadecene copolymer | 0.50 |
| Glycerol | 7.50 |
| Magnesium sulfate | 0.50 |
| Polyol Soluble Licorice Extract P-U | 1.00 |
| Preservative, perfume | q.s. |
| Water | to 100 |

Example No. 16

| | |
|---|---|
| Polyglyceryl-2 dipolyhydroxystearate | 4.50 |
| 2-Ethylhexyl methoxycinnamate | 4.00 |
| 2,4-Bis[4-(2-ethylhexyloxy)-2-hydroxylphenyl]-6-(4-methoxyphenyl)-1,3,5-triazine | 2.50 |

-continued

| | |
|---|---|
| Diethylhexyl butamido triazone | 3.00 |
| Ethylhexyl triazone | |
| 4-Methylbenzylidene camphor | 2.00 |
| Octocrylene | 2.50 |
| Phenylbenzimidazole sulfonic acid | 2.00 |
| Titanium dioxide | 3.00 |
| Paraffinum liquidum | 8.00 |
| Dicaprylyl ether | 7.00 |
| Butylene glycol dicaprylate/dicaprate | 4.00 |
| Phenyl methylpolysiloxane | 2.00 |
| PVP hexadecene copolymer | 1.00 |
| Octoxyglycerol | 0.50 |
| Glycerol | 2.50 |
| Magnesium chloride | 0.70 |
| Tocopheryl acetate | 1.00 |
| Polyol Soluble Licorice Extract P-U | 0.80 |
| Preservative, perfume | q.s. |
| Ethanol | 1.00 |
| Water | to 100 |

Examples of W/O Emulsions

| Example No. 17 | 17 | 18 |
|---|---|---|
| Polyglyceryl-2 dipolyhydroxystearate | 4.00 | 5.00 |
| Lanolin alcohol | 0.50 | 1.50 |
| Isohexadecane | 1.00 | 2.00 |
| Myristyl myristate | 0.50 | 1.50 |
| Vaseline | 1.00 | 2.00 |
| Butyl methoxydibenzoylmethane | 0.50 | 1.50 |
| 4-Methylbenzylidene camphor | 1.00 | 3.00 |
| Butylene glycol dicaprylate/dicaprate | 4.00 | 5.00 |
| Shea butter | — | 0.50 |
| Butylene glycol | — | 6.00 |
| Octoxyglycerol | — | 3.00 |
| Glycerol | 5.00 | — |
| Tocopheryl acetate | 0.50 | 1.00 |
| Polyol Soluble Licorice Extract P-U | 0.2 | 0.1 |
| EDTA | 0.20 | 0.20 |
| Preservative | q.s. | q.s. |
| Ethanol | — | 3.00 |
| Perfume | q.s. | q.s. |
| Water | to 100 | to 100 |

Example (W/O Cream)

Example No. 19

| | |
|---|---|
| Polyglyceryl-3 diisostearate | 3.50 |
| Glycerol | 3.00 |
| Polyglyceryl-2 dipolyhydroxystearate | 3.50 |
| Polyol Soluble Licorice Extract P-U | 0.25 |
| Preservative | q.s. |
| Perfume | q.s. |
| Magnesium sulfate | 0.6 |
| Isopropyl stearate | 2.0 |
| Caprylyl ether | 8.0 |
| Cetearyl isononanoate | 6.0 |
| Water | to 100 |

Example (W/O Emulsion)

Example No. 20

| | |
|---|---|
| Triceteareth-4 phosphate | 0.80 |
| Butylhydroxytoluene | 0.05 |
| Glyceryl lanolate | 1.70 |
| Cyclomethicone | 2.20 |
| Isopropyl palmitate | 1.00 |
| Polyol Soluble Licorice Extract P-U | 0.050 |
| Polyacrylic acid | 0.50 |
| Ethylenediaminetetraacetic acid | 1.00 |
| Sodium hydroxide | q.s. |
| Citric acid | 0.01 |
| Preservative | q.s. |
| Perfum | q.s. |
| Water | to 100 |

What is claimed is:

1. A method of treating skin or caring for the skin of a patient of diabetes mellitus, wherein the method comprises applying to the skin of the patient licochalcone A and/or at least one of a plant extract and a microbiologically obtained extract containing licochalcone A in an amount which is sufficient for treating the skin or caring for the skin.

2. The method of claim 1, wherein skin suffering from at least one of dryness, pruritus, impaired wound healing, reduced skin sensation and infection is treated or cared for.

3. The method of claim 1, wherein licochalcone A and/or the at least one of a plant extract and a microbiologically obtained extract containing licochalcone A is applied in the form of a cosmetic or dermatological preparation.

4. The method of claim 3, wherein the preparation comprises from 0.0001% to 5% by weight of licochalcone A, based on a total weight of the preparation.

5. The method of claim 4, wherein the preparation comprises from 0.001% to 1% by weight of licochalcone A.

6. The method of claim 4, wherein the preparation comprises from 0.005% to 0.15% by weight of licochalcone A.

7. The method of claim 3, wherein the preparation further comprises from 0.001% to 10% by weight of one or more polyols, based on a total weight of the preparation.

8. The method of claim 7, wherein the preparation comprises from 0.01% to 5% by weight of the one or more polyols.

9. The method of claim 7, wherein the preparation comprises from 0.05% to 2% by weight of the one or more polyols.

10. The method of claim 7, wherein the one or more polyols comprise butylene glycol.

11. The method of claim 3, wherein the preparation comprises a plant extract comprising licochalcone A.

12. The method of claim 11, wherein the plant extract comprises an extract of *Radix Glycyrrhizae inflatae*.

13. The method of claim 3, wherein the preparation is an O/W emulsion.

14. The method of claim 13, wherein the preparation is an O/W cream.

15. The method of claim 3, wherein the preparation is a W/O emulsion.

16. The method of claim 15, wherein the preparation is a W/O cream.

17. The method of claim 3, wherein the preparation is a gel.

* * * * *